US012372540B2

(12) United States Patent
Evans et al.

(10) Patent No.: US 12,372,540 B2
(45) Date of Patent: Jul. 29, 2025

(54) DEVELOPMENT OF NOVEL AUTOMATED SCREENING METHOD FOR DETECTION OF FVIII INHIBITORS

(71) Applicant: PRESCIENT MEDICINE HOLDINGS, INC., Hummelstown, PA (US)

(72) Inventors: Matthew Stephen Evans, Manheim, PA (US); Keri Jon Donaldson, Hummelstown, PA (US); Mary Elaine Dye, Hershey, PA (US); Michael H. Creer, Hummelstown, PA (US)

(73) Assignee: PRESCIENT MEDICINE HOLDINGS, INC., Hummelston, PA (US)

( * ) Notice: Subject to any disclaimer, the term of this patent is extended or adjusted under 35 U.S.C. 154(b) by 1137 days.

(21) Appl. No.: 17/151,936

(22) Filed: Jan. 19, 2021

(65) Prior Publication Data
US 2021/0140985 A1 May 13, 2021

Related U.S. Application Data

(63) Continuation of application No. 15/572,085, filed as application No. PCT/US2016/031324 on May 6, 2016, now abandoned.
(Continued)

(51) Int. Cl.
*G01N 33/86* (2006.01)
(52) U.S. Cl.
CPC ....... *G01N 33/86* (2013.01); *G01N 2333/755* (2013.01); *G01N 2800/52* (2013.01)

(58) Field of Classification Search
CPC ............ G01N 33/86; G01N 2333/755; G01N 2800/52
See application file for complete search history.

(56) References Cited

U.S. PATENT DOCUMENTS

| 5,576,291 A | 11/1996 | Curtis et al. |
| 2014/0134151 A1 | 5/2014 | Lu et al. |
| 2015/0111235 A1 | 4/2015 | Nakamura et al. |

FOREIGN PATENT DOCUMENTS

| JP | 10508945 | 9/1998 |
| WO | 2009153964 | 12/2009 |
| WO | 2015013495 | 1/2015 |

OTHER PUBLICATIONS

Lusher, Jeanne M., et al. "Recombinant factor VIII for the treatment of previously untreated patients with hemophilia A—safety, efficacy, and development of inhibitors." New England journal of medicine 328.7 (1993): 453-459. (Year: 1993).*

(Continued)

*Primary Examiner* — Olivia M. Wise
*Assistant Examiner* — Mary C Leverett
(74) *Attorney, Agent, or Firm* — Womble Bond Dickinson (US) LLP

(57) ABSTRACT

Disclosed herein are methods for determining the presence of a coagulation inhibitor in a patient. A patient curve associated with the patient sample and having a patient slope (Ps) and a a standard curve associated with a control sample and having a control slope (Cs) are generated, and the Ps and the Cs are compared to obtain a Ps/Cs parallelism ratio. A Ps/Cs parallelism ratio of less than a predetermined ratio is indicative of presence of a coagulation inhibitor in the patient sample.

16 Claims, 3 Drawing Sheets

Related U.S. Application Data

(60) Provisional application No. 62/157,709, filed on May 6, 2015.

(56) References Cited

OTHER PUBLICATIONS

Lawrie, A. S., et al. "Assay of plasma clotting factors using parallel-line bioassay principles." Sysmex Journal International 13.1 (2003): 37-42. (Year: 2003).*
Kempton, Christine L., and Gilbert C. White. "How we treat a hemophilia A patient with a factor VIII inhibitor." Blood, The Journal of the American Society of Hematology 113.1 (2009): 11-17. (Year: 2009).*
Gouw, Samantha C., et al. "Factor VIII products and inhibitor development in severe hemophilia A." New England Journal of Medicine 368.3 (2013): 231-239. (Year: 2013).*
M. S. Evans et al, "Development of a Novel Automated Screening Method for Detection of FVIII Inhibitors", International Journal of Laboratory Hematology, 2017 John Wiley & Sons Ltd, Int. Jni Lab. Hem. 2017, 39, 185-190.
Charles R M Hay et al, "The diagnosis and management of factor VIII and IX inhibitors: a guideline from the United Kingdom Haemophilia Centre Doctors Organisation", 2006 Blackwell Publishing Ltd, British Journal of Haematology, 133, 591-605.
Evans Matthew S et al, "Development of a Novel Automated Screening Method for Detection of FVIII Inhibitors", Blood Journal, 2004 The American Cancer Society of Hematology, vol. 124, No. 21,1-5.
European Search Report for Application No. 16790197.4, Nov. 30, 2018.
Office Action for Japanese Application No. 2018-510328, Nov. 28, 2018.
Duncan et al., Haemostasis: Methods and Protocols, Nijmegan-Bethesda Assay to Measure Factor VIII Inhibitors; pp. 321-333, Jan. 1, 2013.
EPO Examination Report for EP Application No. 16790197.4, May 28, 2020.
Glund, et al. "Idarucizumab, a Specific Antidote for Dabigatran: Immediate, Complete and Sustained Reversal of Dabigatran Induced Anticoagulation in Elderly and Renally Impaired Subjects", Blood 2014, 124(21):344, Retrieved from http://www.bloodjournal.org/content/124/21/344.
PCT/US2016/031324, International Search Report and Written Opinion dated Aug. 19, 2016.
Over, J.; "Methodology of the one-stage assay of factor VIII(VIII:C)"; Scand J Haematol; vol. 33; Issue 41 (Dec. 1982); p. 13-24. (Year: 1982).
Curtis, AD. The statistical evaluation of factor VIII clotting assays. Scand J Haematol 1984; 33(Suppl. 41): 55-68. (Year: 1984).
Funk, D. M.; "Coagulation assays and anticoagulation monitoring"; Hematology Am Soc Hematol Educ Program (2012) 2012 (1): 460-465. (Year: 2012).
Yeh, C. H. et al.; "Evolving of new oral anticoagulants for treatment of venous thromboembolism"; Blood, Aug. 14, 2014; vol. 124; No. 7; p. 1020-1028. (Year: 2014).
Baglin, T. et al.; "Effects on routine coagulation screens and assessment of anticoagulant intensity in patients taking bral dabigatran or rivaroxaban: Guidance from the British Committee for Standards in Haematology"; British Journal of Haematology, 2012, 159, 427-429 (Year: 2012).
Mackie, I. et al.; "Guidelines on the laboratory aspects of assays used in haemostasis and thrombosis"; Int J Lab Hematol. 2013;35: 1-13 (Year: 2013).

* cited by examiner

DEVELOPMENT OF NOVEL AUTOMATED SCREENING METHOD FOR DETECTION OF FVIII INHIBITORS

CROSS-REFERENCE TO RELATED APPLICATIONS

This application is a continuation of U.S. Non-Provisional application Ser. No. 15/572,085, filed Nov. 6, 2017, which is a national stage of International Application No. PCT/US2016/031324, filed May 6, 2016, which claims the priority to and the benefit of U.S. Provisional Application No. 62/157,709, filed May 6, 2015, all incorporated herein by reference in their entireties.

FIELD OF INVENTION

The present disclosure relates generally to the field of blood coagulation and more particularly to identification of coagulation inhibitors in patient samples.

BACKGROUND

Factor VIII (FVIII) activity is determined by directly measuring the activated partial thromboplastin time (APTT) of a patient plasma sample and determining the percent activity from a standard curve generated from plotting the measured clotting time (in seconds) on a semi-log scale vs a known percent activity of the standard at several specific dilution points. Factor VIII activity for the patient samples is then performed on dilutions of patient plasma mixed with equal amounts of plasma deficient in the factor to be measured, and the percent of factor in the patient plasma is calculated from the standard curve by plotting the observed clotting time for a specific dilution of the patient sample. Prior to the present disclosure, to minimize the potential for under-reporting an activity level or missing the presence of an inhibitor, a subjective assessment of parallelism of the patient curve to the standard curve is performed. In absence of an inhibitor the standard and patient curves are parallel to each other with the patient curve's slope (Ps) similar to the standard curve's slope (Cs). In patients with an inhibitor, the clotting time is prolonged. Furthermore, with each subsequent dilution, the amount of inhibitor is diluted out, leading to shorter clotting times for subsequent dilutions. In practice this leads to a less steep patient curve slope (Ps) compared to the standard curve slope (Cs) and thus nonparallel lines. Parallelism determination is currently a subjective assessment that leads to increased error in reporting, potential missed evaluation for inhibitors, and potential unnecessary testing for inhibitors.

SUMMARY

Disclosed herein are methods addressing the shortcomings of the art, and may provide any number of additional or alternative advantages, such as providing an objective and automated tool to assess parallelism as an added screening tool for the presence of a Factor VIII inhibitor.

Certain embodiments of the invention include a method for determining the presence of a Factor VIII inhibitor in a patient sample. The method includes the steps of: generating a patient curve associated with a patient sample and having a patient slope (Ps); generating a standard curve associated with a control sample and having a control slope (Cs), and comparing the Ps and the Cs to obtain a Ps/Cs parallelism ratio, wherein a Ps/Cs parallelism ratio of less than 0.45 is indicative of presence of a Factor VIII inhibitor in the patient sample. The method further includes the Ps and Cs curves being generated by plotting a plurality of clotting time points for a series of dilutions of the patient sample and the control sample relative to the FVIII clotting activity. The Ps/Cs parallelism ratio is determined by a microprocessor in electronic communication with a clotting detection machine. In certain embodiments, the method further includes determining the ratio of less than 0.45 and administering to the patient at least one agent for treatment of a condition associated with the presence of the Factor VIII inhibitor. In certain embodiments, the condition is hemophilia A. In certain embodiments, the condition is an autoimmune disorder. In certain embodiments, the agent is one or more of the following: human factor VIII, porcine factor VIII, and an FVIII bypassing agent. In certain embodiments, the method further includes producing an output by the microprocessor, the output being capable of perceived visually or audibly by a human user or as digital information readable by a computer, wherein the output comprises an indication of the Ps/Cs ratio.

Certain embodiments of the invention include a method of determining the presence of a coagulation inhibitor in a bodily fluid of a patient. The method includes the steps of detecting whether a coagulation inhibitor is present in the patient sample by generating a patient curve associated with the patient sample and having a patient slope (Ps) and generating a standard curve associated with a control sample and having a control slope (Cs). The Ps and Cs curves are generated by plotting a plurality of clotting time points for a series of dilutions of the patient sample and the control sample relative to the clotting activity. The method includes the steps of comparing the Ps and the Cs to obtain a Ps/Cs parallelism ratio, wherein a Ps/Cs parallelism ratio of less than a predetermined ratio is indicative of presence of a coagulation inhibitor in the patient sample. In certain embodiments, the predetermined ratio is about 0.45. In certain embodiments, the coagulation inhibitor is dabigatran. In certain embodiments, the coagulation inhibitor is Factor VIII inhibitor. In certain embodiments, the coagulating agent is mammalian Factor VIII.

Certain embodiments of the invention include a method of determining the presence of an anti-coagulating compound in a bodily fluid of a patient and treating such patient. The method includes the steps of obtaining a patient sample of the bodily fluid; detecting whether an anti-coagulating compound is present in the patient sample; and administering an effective amount of coagulating agent to the patient, in response to a Ps/Cs parallelism ratio being less than a predetermined ratio. The Ps/Cs parallelism ratio is determined by generating a patient curve associated with the patient sample and having a patient slope (Ps); generating a standard curve associated with a control sample and having a control slope (Cs), and the Ps and Cs curves being generated by plotting a plurality of clotting time points for a series of dilutions of the patient sample and the control sample relative to the clotting activity; and comparing the Ps and the Cs to obtain a Ps/Cs parallelism ratio. In certain embodiments, the predetermined ratio is about 0.45. In certain embodiments, the anti-coagulating compound is Factor VIII inhibitor. In certain embodiments, the coagulating agent is mammalian Factor VIII. In certain embodiments, the anti-coagulating compound is dabigatran. In certain embodiments, the anti-coagulating compound is rivaroxaban.

Numerous other aspects, features and benefits of the present disclosure may be made apparent from the following detailed description taken together with the drawing figures. The methods of detection and treatment described herein can include compounds described herein, other components, or ingredients depending on desired prevention and treatment goals. It should be further understood that both the foregoing general description and the following detailed description are exemplary and explanatory and are intended to provide further explanation of the invention as claimed.

BRIEF DESCRIPTION OF FIGURES

The present disclosure can be better understood by referring to the following figures that illustrate certain the principles of the disclosure.

DETAILED DESCRIPTION

Figure 1:
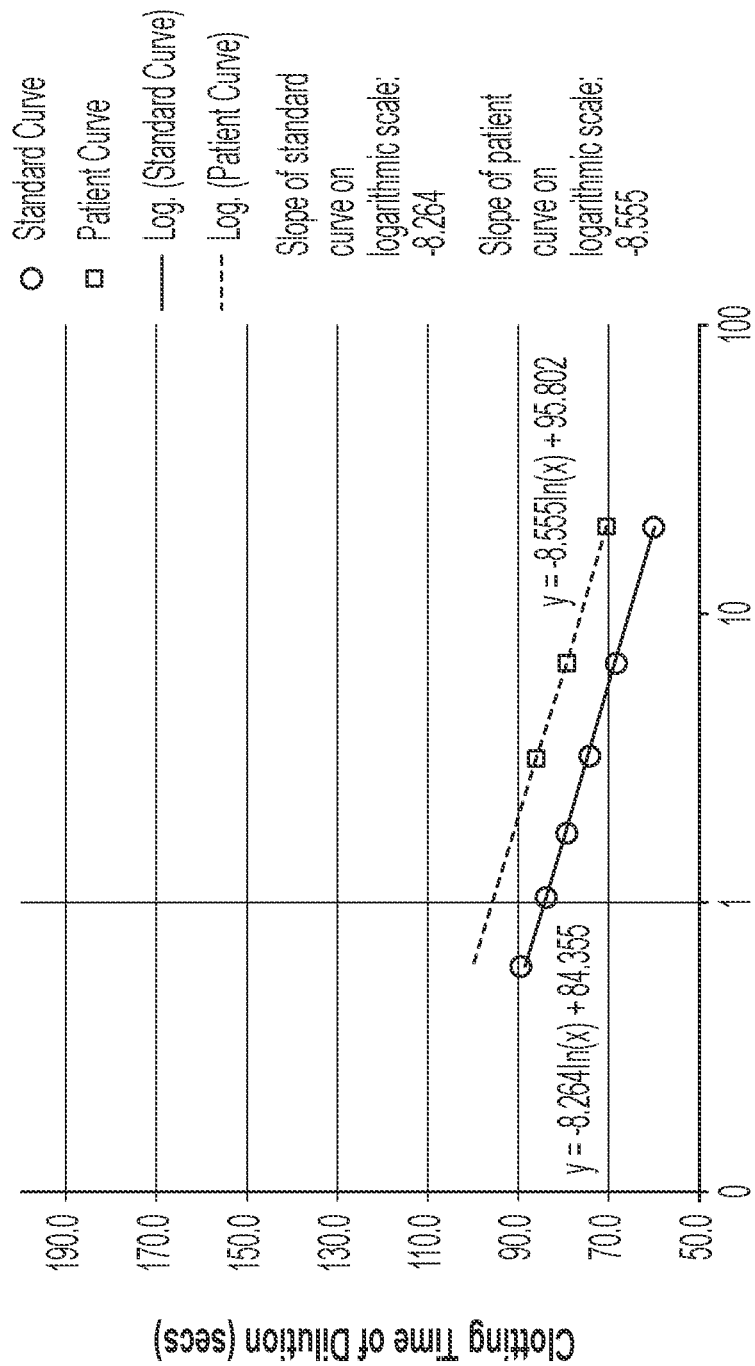
FIG. 1 is an example of parallelism curve with parallel curves obtained from analysis of biological samples obtained from a patient without inhibitor.

Reference will now be made to the exemplary embodiments illustrated in the drawings, and specific language will be used here to describe the same. It will nevertheless be understood that no limitation of the scope of the invention is thereby intended. Alterations and further modifications of the inventive features illustrated here, and additional applications of the principles of the inventions as illustrated here, which would occur to one skilled in the relevant art and having possession of this disclosure, are to be considered within the scope of the invention. For purposes of interpreting this specification, the following definitions will apply and whenever appropriate, terms used in the singular will also include the plural and vice versa. In the event that any definition set forth below conflicts with any document incorporated herein by reference, the definition set forth below shall control.

As used in this specification and the appended claims, the singular forms "a," "an" and "the" include plural referents unless the context clearly dictates otherwise. Thus, for example, reference to "a protein" or an "antibody" includes a plurality of proteins or antibodies, respectively; reference to "a cell" includes mixtures of cells, and the like.

A sample refers to bodily fluids from a patient or a healthy individual or a fluid specimen that serves as a control for the methods disclosed herein. Non-limiting examples of a sample include blood, plasma, serum, blood extracts, or other blood products.

A predetermined ratio refers to a parallelism ratio standardized for a particular embodiment of the invention, and is determined, in many instances, by standardizing the reagents, reaction conditions, and instrumentation to evaluate samples.

The disclosure herein relates to improved, automated methods for identification of coagulation inhibitors in patient samples, and in particular for Factor VIII (FVIII) inhibitors. The disclosure accordingly provides methods and systems for use in determining whether a patient sample contains a FVIII inhibitor, and can accordingly be used for diagnosis, or to aid in the diagnosis of a disease or other condition in an individual that is associated with FVIII inhibition.

Briefly, Factor VIII is a well-known clotting factor with a very low normal plasma concentration of approximately 0.0007 µmol/L. It circulates as inactive plasma protein in a number of distinct fragmented species in a tightly associated complex with von Willebrand factor. Factor VIII activation occurs in the blood typically in response to an injury to a blood vessel. Activation comprises cleavage of FVIII between its A1 and A2 domains, resulting in an unstable heterotrimeric Factor VIIIa molecule. Factor VIIIa interacts with Factor IX with a subsequent, well characterized series of reactions that result in blood clot formation.

The present disclosure relates in part to detection of inhibitors that limit the capability of FVIII to participate in the cascade of events that culminate in blood clotting. In certain embodiments, a FVIII inhibitor as the term is used herein can refer to a congenital deficiency of FVIII, or an acquired FVIII deficiency. Such inhibitors include but are not necessarily limited to antibodies that bind with specificity to at least one epitope present on FVIII and/or FVIIa. In embodiments, the inhibitor comprises alloantibodies to FVIII, such as in the case of an individual that has developed an antibody response to FVIII as a result of receiving blood or another FVIII-containing composition from a different individual, which occurs in, for example, some congenital hemophilia A patients. In an embodiment, the inhibitor can comprise an autoantibody to FVIII, such as in the case of an individual with, or at risk for developing acquired hemophilia. Such an individual may develop the autoantibodies and the hemophilia condition after birth, and often much later in life. It will therefore be recognized that the present disclosure is suitable for determining FVIII inhibitors in individuals who have alloantibodies that inactivate FVIII, which typically occurs in direct proportion to their concentration (first-order kinetics), or acquired inhibitors/autoantibodies which typically show a non-linear inactivation pattern (type II or second-order kinetics). Additional applications of this technology could allow identification and classification of lupus anticoagulants, and allow rapid classification of the specific anticoagulant in the sample. Prior to the present disclosure this testing typically takes days to weeks and requires additional sub-specialty testing and expertise.

Existing approaches for determining FVIII inhibitors using clot-based methods are well known in the art. For example, see Ellinor, et al., *Laboratory Assessment of Factor VIII Inhibitor Titer*, Am J Clin Pathol (2009); Vol. 131:552-558. The so-called the Bethesda clot-based assay is the most commonly used laboratory test to quantify FVIII antibodies in patient plasma. The typical Bethesda method results in a quantification of FVIII activity that is present after the patient's plasma, or serial dilutions of patient plasma, is mixed with equal parts of control plasma, such as normal pooled plasma (NPP), which provides functional FVIII. A positive control mixture that is used to control for FVIII instability is prepared using NPP. Stocks of buffered normal pooled plasma for use in making a 1:1 mix with patient plasma are commercially available. The mixtures are typically incubated a 37° C. for about 120 minutes during which the inhibitor, if present in the patient sample, neutralizes FVIII. Results from the patient sample and positive sample are compared. A modified version of the Bethesda method, i.e, the so-called "Nijmegen" modification, provides increased specificity for low-titer FVIII inhibitor measurements by buffering the pH of the patient and control mixtures with imidazole, and using FVIII-deficient plasma in the control mixture and patient dilutions.

As those skilled in the art will recognize, a Bethesda unit (BU) is defined as the amount of antibody or other inhibitor that neutralizes in a plasma sample 50% of 1 unit of factor VIII:C in normal plasma after a 120 minute incubation at 37° C. In more detail, BU is calculated using doubling dilutions of patient plasma, ranging from 1:2-1:1024, in an imidazole containing buffer, and are incubated with an equal volume of NPP. In a typical circumstance, NPP will comprise approximately 100 IU/dl (1 IU/ml or 100%) of factor VIII. A control that contains an equal volume of normal plasma mixed with buffer is used to establish the 100% value, or as discussed above for the Nijmegen modification, immunodepleted factor VIII deficient plasma is used to establish the 100% value. At the end of the 2 hour heated incubation period residual factor VII activity is determined. This is typically is performed using a standard single stage Activated Partial Thromboplastin Time (APIT) assay with the control as the 100% standard. APTT is also known in the art as the Kaolin Cephalin Clotting Time (KCCT) and the Partial Thromboplastin Time with Kaolin (PTTK). These assays are well known in the art. In general, APTT is performed by addition of phospholipid (cephalin) and a contact activator (e.g. Kaolin, micronized silica or ellagic acid) to platelet poor plasma, followed by addition of calcium, which initiates clotting, which is the point when timing of clotting is initiated. The APTT is the time taken from the addition of calcium to the formation of a fibrin clot. Most laboratories employ an automated method for determining APTT, wherein clot formation is deemed to have occurred when the optical density of the mixture has exceeded a certain threshold. The inhibitor concentration is then calculated from a graph constructed to show residual factor VII activity versus inhibitor units.

Factor VIII activity is determined by directly measuring the activated partial thromboplastin time of a patient plasma sample and determining the percent activity from a standard curve generated from plotting the measured clotting time (in seconds) on a semi-log scale vs a known percent activity of the standard at several specific dilution points. This accordingly provides a line with a particular slope. A control line (Cs) is compared to a patient line (Ps) to determine parallelism between the two lines. As also described further below in the Example, prior to the present disclosure, the parallelism determination was made subjectively and without specific cut-off parameters for segregating patients, which created significant risk for erroneous interpretation and result reporting. This has been solved by an embodiment of the invention described further in the Example below. Briefly, we compared the ratio of the slope of the curve generated from patient dilutions without detectable inhibitor (representing a disease-free state) and the slope of the curve generated from patient dilutions with a known inhibitor (representing disease state), versus the slope of the standard curve. We confirmed presence of an inhibitor for each patient sample by Bethesda assay utilizing the Nijmegen modification. Using a bell curve generated from a parameter simulation of obtained Ps/Cs ratios with and without an inhibitor, we determined a ratio of Ps/Cs of 0.45 to be a cut-off that is 100% sensitive and 80% specific for detection of an inhibitor. Thus, the present disclosure demonstrates based on the available statistics that, if the ratio of the Ps/Cs curves is <0.45, there is 100% chance that an inhibitor is present in the sample. Accordingly, in certain embodiments a ratio of the Ps/Cs curves of <0.45 is indicative that the individual from whom the sample was obtained is in need of treatment for a condition associated with the presence of the FVIII inhibitor. If desired, further characterization of the type of inhibitor can be performed. In embodiments, further testing is performed to determine heparin contamination and/or the presence of lupus anticoagulant. Additional inhibitor identification classification, and anticoagulant drug classification will occur in the same process, with the ratio of the slopes being used to categorize both the presence and absence of the drug and type of agent present. Certain embodiments of the invention can be used to distinguish between nonspecific clotting inhibitors such as lupus anticoagulants or specific clotting factor inhibitors, such as specific oral anticoagulants.

In embodiments, the disclosure includes determining a ratio of Ps/Cs curves of <0.45 for an individual, and administering to the individual at least one agent for therapy of a disorder or condition associated with the present of the inhibitor in the individual. In embodiments, determining a ratio of Ps/Cs curves of <0.45 is used to diagnose, or aid in a physician's diagnosis of a disorder. In embodiments, the disorder comprises a congenital disorder, such as congenital Hemophilia A. or development of acquired factor VIII inhibitors, such as acquired Hemophilia A.

In embodiments, the disclosure comprises determining a ratio of Ps/Cs curves of <0.45, diagnosing the patient with a disorder associated with the presence of at least one factor VIII inhibitor, and administering to the individual at least one exogenous agent for treating the disorder. In embodiments, the individual is diagnosed with Hemophilia A, and is administered an agent for treating Hemophilia A.

In embodiments, testing a sample from an individual according to this disclosure and determining a ratio of Ps/Cs curves of <0.45, and diagnosing the patient with a disorder associated with the presence of at least one factor VIII inhibitor, is followed by administering to the individual at least one exogenous agent for treating the disorder. In embodiments, the agent is selected from 1-deamino-8-d-arginine vasopressin, an infusion of human or porcine factor VIII, an FVIII bypassing agent, such as an activated prothrombin complex concentrate, Xa or VIIa, including recombinant versions thereof, of the individual is administered an agent (or subjected to a process) for use in inhibitor elimination, or an agent used for immunosuppression. In embodiments, an extracorporeal approach is used to, for example, remove autoantibodies to FVIII, such as with a plasmapheresis or immunoadsorption approach. In embodiments, inhibitor reduction or elimination is used for bleeding patients, or patients who are scheduled for a surgical intervention, and who have high titer inhibitors and/or have failed to respond to bypassing agents. In certain approaches, following an extracorporeal approach to reduce or eliminate the inhibitor(s), the individuals are given FVIII replacement, such as an amount of FVIII effective to achieve hemostasis.

In certain embodiments, testing a sample from an individual according to this disclosure and determining a ratio of Ps/Cs curves of <0.45, and diagnosing the patient with a disorder associated with the presence of at least one factor VIII inhibitor, is followed by administering to the individual at least one immunosuppression agent, such as prednisolone. In embodiments, the immunosuppression agent can be combined with another agent intended to enhance its effect, such as cyclophosphamide, azathioprine, vincristine, mycophenolate mofetil, 2-chlorodeoxyadenosine, Cyclosporine A, and combinations thereof.

In certain embodiments, testing a sample from an individual according to this disclosure and determining a ratio of Ps/Cs curves of <0.45, and diagnosing the patient with a disorder associated with the presence of at least one factor VIII inhibitor, is followed by administering to the individual intravenous immunoglobulin (IVIG). In embodiments, the individual can also be treated with a targeted biologic therapy, such as rituximab, alone or in combination with other agents, such as prednisone and/or cyclophosphamide.

The method of this disclosure may be performed on an assay system or blood analyzer. Such a device may perform an assay or other measurements, send information to a data processing apparatus, analyze the information, and display, print, or otherwise send results or other information determined during the analysis. Examples of machines on which the method may be performed include, as non-limiting examples, the STA-R Evolution (manufactured by Diagnostica Stago) or blood coagulation analyzers such as the CA-1500, CA-660, CS-2011i, or CS-5100 (manufactured by Sysmex UK LTD). Exemplary systems are described in U.S. Pat. Nos. 7,720,880, 7,085,669, the disclosures of each of which are all incorporated herein by reference.

In embodiments, the method of the disclosure is carried out using a machine in electronic communication with a microprocessor programmed to generate a ratio of Ps/Cs curves, and to identify samples that segregate on either side of the 0.45 threshold described herein. In embodiments, the disclosure comprises receiving an input of digitized data corresponding BUs for at least one patient sample and at least one control sample; plotting the digitized data to obtain a Ps and Cs curve; calculating a Ps/Cs ratio from the digitized data, and providing an indication of the Ps/Cs ratio as a user-recognizable output. In embodiments, the user-recognizable output is provided by a device selected from the group consisting of a visual display, a printer, an output data port, an RF transmitter, and digital medium storage device.

In various embodiments, the disclosure comprises fixing in a tangible medium the ratio of Ps/Cs curves. The tangible medium can be any type of tangible medium, such as any type of digital medium, including but not limited to a DVD, a CD-ROM, a portable flash memory device, or a printed or digitized report, etc., such as a spreadsheet or word processing document. The disclosure includes providing the tangible medium to a health care provider to assist with development of a diagnosis and/or recommendation for treatment of the individual and/or for developing a prognosis for the individual, such as for treating hemophilia or any other disorder associated with the presence of FVIII inhibitor(s).

In certain embodiments, the disclosure includes sequential testing of samples from an individual over a period of time, such as a treatment period to monitor the progress of a therapeutic approach intended for treating hemophilia or any other disorder associated with the presence of FVIII inhibitor(s), and/or to determine whether the amount of inhibitors is the individual is being reduced and/or neutralized during the course of any particular therapy.

One of the most serious adverse complications of Hemophilia A treatment is the development of antibodies to factor VIII, most commonly alloantibodies to transfused factor VIII in patients with known factor VIII deficiency. Inhibitors occur in up to 25-30% of patients with severe hemophilia A and in 3-13% of those with mild hemophilia. While the majority of factor VIII inhibitors arise in patients with severe hemophilia, an increasing concern is that nearly 30% of new inhibitors that are being diagnosed arise in patients with mild hemophilia leading to bleeding symptoms more characteristic of severe hemophilia.

Most inhibitors in persons with severe hemophilia A develop early in treatment during the first 50 exposure days, with an overall risk estimated to be 36% in first 18 exposure days of those with severe disease. In contrast, most inhibitors in persons with mild hemophilia develop later in life, commonly after an episode of intensive treatment with FVIII concentrates for surgery or trauma.

In patients with severe hemophilia, who develop inhibitors, the primary clinical manifestation is decreased response to infused factor. Those on prophylactic factor infusions may develop more breakthrough bleeding or less response to infusions for acute bleeding events. In patients with mild hemophilia, development of inhibitors may also lead to a decreased response to endogenous factor, causing development of a more severe phenotype.

When an inhibitor is suspected, the clinical laboratory must perform cumbersome, time-consuming assays for confirmation. Traditionally, this has been by the Bethesda assay. The intricacies of this assay to detect inhibitors, and the implications for inhibitor development in patients with hemophilia, highlight the value of this newly developed automated screening assay, which can be easily applied to one stage aPTT based FVIII assays. Methods described herein can detect the presence of both endogenous and exogenous inhibitors to clotting factors other than FVIII.

In addition to the clinical benefits of the invention, the logistical implications are highlighted by the fact that the assays described herein leverage routine factor clotting assays to provide an objective screening method for the presence of an inhibitor, which can easily be applied to any coagulation system platform. Embodiments of the invention can also screen for the detection of inhibitors to other specific clotting factors or lupus anticoagulants. Embodiments of the invention can also screen for the presence of an inhibitor effect in patients, who present with bleeding or recurrent venous thromboembolism while on the newer oral anticoagulants which directly inhibit Factor Xa and thrombin.

Certain embodiments of the method include determining the presence of an anti-coagulating compound in a bodily fluid of a patient and treating such patient. The method includes the steps of obtaining a patient sample of the bodily fluid and detecting whether an anti-coagulating compound is present in the patient sample. The presence of the anti-coagulating compound is detected by generating a patient curve associated with the patient sample and having a patient slope (Ps); generating a standard curve associated with a control sample and having a control slope (Cs), and comparing the Ps and the Cs to obtain a Ps/Cs parallelism ratio. The Ps and Cs curves are generated by plotting a plurality of clotting time points for a series of dilutions of the patient sample and the control sample relative to the FVIII clotting activity. The Ps/Cs parallelism ratio being less than a predetermined ratio is indicative of the presence of an anti-coagulating compound in the patient. An effective amount of coagulating agent is then administering to the patient. Embodiments of the methods could also be used to screen patients on the new target specific oral anticoagulants.

The impact of venous thromboembolism in the United States is highlighted by the fact that there are 300,000 to 600,000 new cases each year with up to a 12% death rate within one month in those diagnosed with a pulmonary embolism. This has generated a market for target specific oral anticoagulants that directly target thrombin (dabigatran) or Factor Xa (rivaroxaban, apixaban, edoxaban). Recent research indicates an increase in the PT and APTT, and decreased activity for factors II, V, VII, VIII, IX, X and XI. For dabigatran, thrombin time has been shown to be prolonged in a dose dependent manner, but is excessively sensitive. Currently existing assays cannot quickly screen for presence of any one of these agents. For example, patients on a direct acting oral anticoagulant, who require emergent procedures and surgeries, may be unaware or unable to communicate what anticoagulant they are on and/or when their last dose was taken. An embodiment of the invention can include an automated screening assay to rapidly screen for the presence of any of these anticoagulants in a patient sample. For example, if dabigatran is identified and a reversal of bleeding is needed, one can use a specific coagulating agent such as idarucizumab. Depending on the needs of the patient and the specific treatment protocols, one can also use activated Prothrombin Complex Concentrate (FEIBA). Certain situations may involve treatment protocols such as hemodialysis, with or without antifibrinolytic agents. In another example, if rivaroxaban, apixaban or edoxaban (factor Xa inhibitors) are identified and a reversal of bleeding is needed, on can use nonactivated Prothrombin Complex Concentrate (Kcentra). Depending on the needs of the patient and the specific treatment protocols, one may also use antifibrinolytics or targeted anticoagulants such as Andexanet.

Detection and measurement of platelet function is important for identifying patients with platelet dysfunction or hyperfunction, and also monitoring antiplatelet therapies. Embodiments of the invention can also be deployed in evaluating platelet function and presence of anti-platelet agents. Certain embodiments of the method include determining the presence of an antiplatelet agents in a bodily fluid of a patient. The method includes the steps of obtaining a patient sample of the bodily fluid and detecting whether an antiplatelet agent is present in the patient sample. The presence of the antiplatelet agent is detected by generating a patient curve associated with the patient sample and having a patient slope (Ps); generating a standard curve associated with a control sample and having a control slope (Cs), and comparing the Ps and the Cs to obtain a Ps/Cs parallelism ratio. The Ps and Cs curves are generated by conducting platelet function tests. Platelet function tests may include one or more of Platelet Aggregation Studies (PFT) or Platelet Function Assay (PFA). Examples of platelet function tests include, without limitation, one or more of the following: closure time assay, viscoelastometry, bleeding time, platelet aggregation studies, or flow cytometry.

The class of antiplatelet drugs include irreversible cyclooxygenase inhibitors, adenosine diphosphate (ADP) receptor inhibitors, phosphodiesterase inhibitors, protease-activated receptor-1 (PAR-1) antagonists, glycoprotein IIB/IIIA inhibitors, adenosine reuptake inhibitors, and thromboxane inhibitors. Examples of irreversible cyclooxygenase inhibitors include aspirin and Triflusal (Disgren). Examples of adenosine diphosphate (ADP) receptor inhibitors include Clopidogrel (Plavix), Prasugrel (Effient), Ticagrelor (Brilinta), and Ticlopidine (Ticlid). Examples of Phosphodiesterase inhibitors include Cilostazol (Pletal). Examples of protease-activated receptor-1 (PAR-1) antagonists include Vorapaxar (Zontivity). Examples of glycoprotein IIB/IIIA inhibitors (intravenous use only) include Abciximab (ReoPro), Eptifibatide (Integrilin), and Tirofiban (Aggrastat). Examples of adenosine reuptake inhibitors include Dipyridamole (Persantine). Examples of thromboxane inhibitors include thromboxane synthase inhibitors and thromboxane receptor antagonists (Terutroban).

The following example is provided to illustrate the invention, but is not intended to be limiting in any way.

Example 1

As discussed above, typical Factor VIII assays determine Factor VIII activity (in percentage) from a standard curve. This standard curve is generated from plotting measured clotting time (in seconds) versus a known percent activity for the standard at several dilution points. Factor VIII activity for patient samples are then performed on dilutions of patient plasma mixed with equal amounts of known factor deficient plasma, and the percent of factor in the patient plasma is calculated from this standard curve by plotting the observed clotting time for a specific dilution of the patient sample. In order to minimize the potential for under-reporting an activity level or missing presence of an inhibitor substance, the line given by the clotting times of the dilutions of the patient plasma should parallel that given by the dilutions of the system control plasma when plotted on a logarithmic scale.

Figure 2:
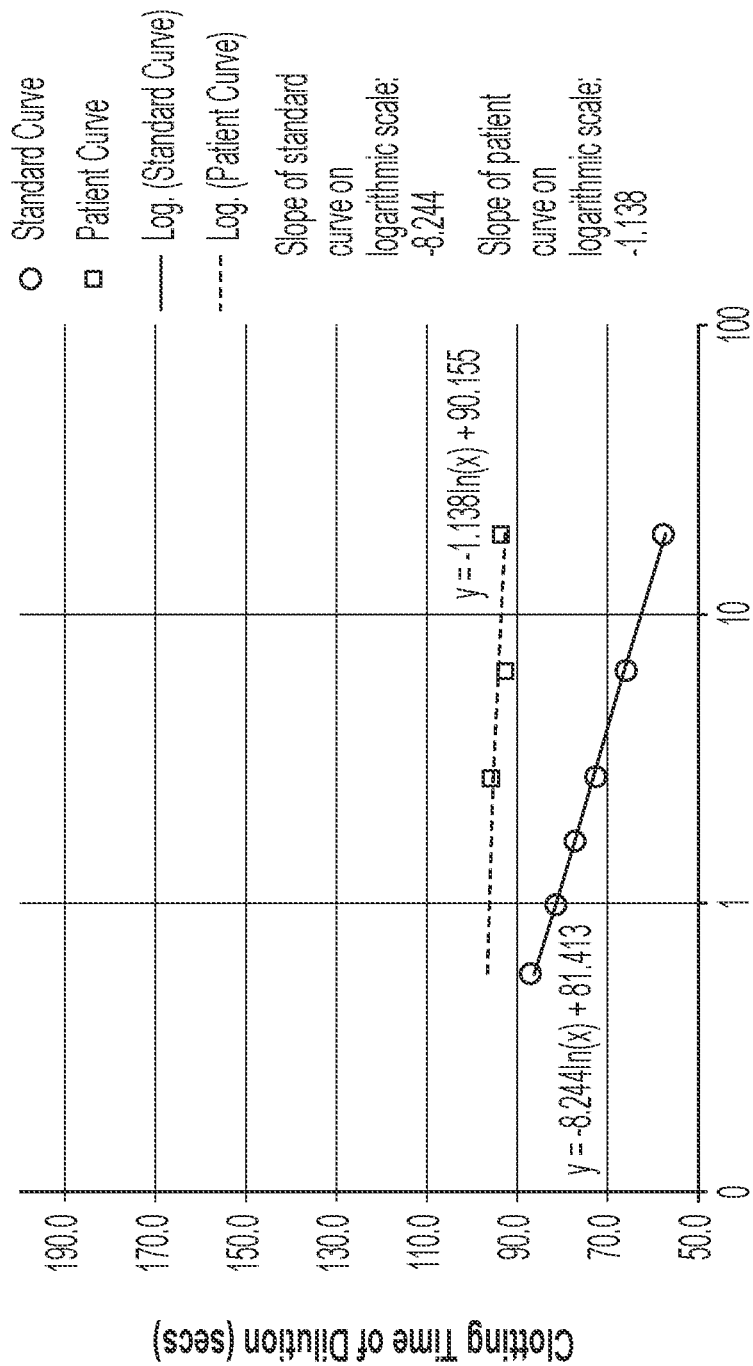
FIG. 2 is an example of parallelism curve with non-parallel curves obtained from analysis of biological samples obtained from a patient with inhibitor.

In absence of inhibitor (disease-free state), the standard and patient curves are parallel to each other with the patient's slope (Ps) similar to the slope of a standard curve (Cs) (FIG. 1). In patients with inhibitor (disease state), the clotting time is prolonged. With each subsequent dilution, the amount of inhibitor is diluted out, leading to shorter clotting times for subsequent dilutions. In practice this leads to a less steep slope (Ps) compared to the standard curve slope (Cs) (FIG. 2). Prior to the present disclosure, determination of "parallelism" was a subjective assessment that led to increased errors in reporting, potential missed evaluation for inhibitors and potential unnecessary inhibitor testing.

We performed Factor VII assays (Low Factor VIII assay modification on STA Compact using low curve calibration at 1:6, 1:15 and 1:30 dilution (STA Deficient VIII, Immuno-Depleted Plasma for Factor VIII:C assay by STA) at appropriate dilutions on Factor VIII deficient hemophilia patients. We examined curves for parallelism by comparing the ratio of the slope of the curve generated from patient dilutions without detectable inhibitor (disease-free state) and the slope of the curve generated from patient dilutions with a known inhibitor (disease state) versus the slope of the standard curve. We confirmed presence of an inhibitor for each patient sample by Bethesda assay utilizing the Nijmegen modification.

Figure 3:
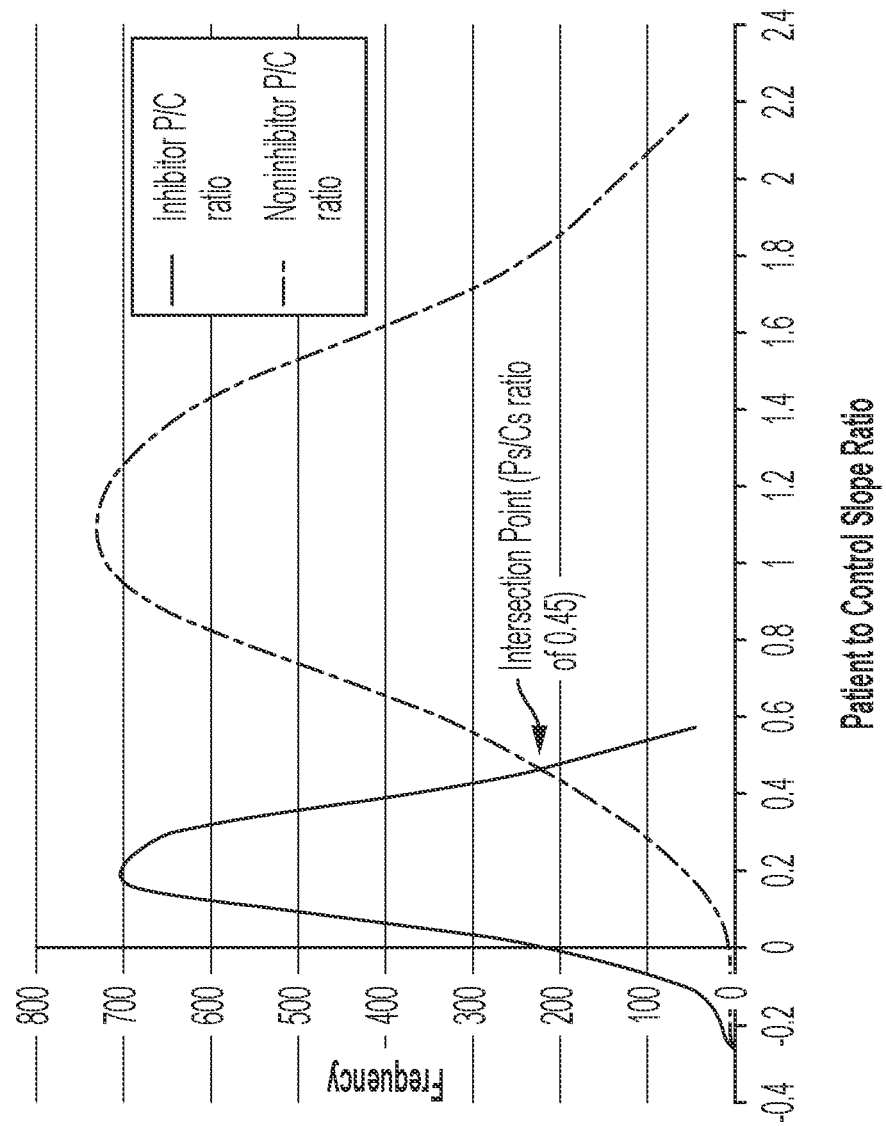
FIG. 3 is an example of a bell curve generated according to an embodiment.

Using a bell curve generated from a parameter simulation of obtained Ps/Cs ratios from screening 21 samples with and without an inhibitor, we determined a ratio of Ps/Cs of 0.45 to be a cut-off that was 100% sensitive and 80% specific for detection of an inhibitor. (FIG. 3). Thus, if the ratio of the curves are <0.45 (see vertical bar in FIG. 3), there is 100% chance that an inhibitor is present in the sample. However, we recognized based on these bell curves that a small percentage of patients with inhibitors could be missed with a larger sample size. Thus, to confirm the validity of this cut-off, we screened 48 de-identified samples with and without low FVIII inhibitor (Bethesda titers <5) obtained from the NHLBI biologic specimen and data repository. In this larger sample set, our cut-off ratio of <0.45 for the detection of an inhibitor to FVIII was 100% sensitive and 91.6% specific, with a positive predictive value of 92.3% and a negative predictive value of 100%. (Tables 1 and 2).

TABLE 1

Results of Inhibitor Screen Using Ratio of Patient to Control Slopes
(Ps/Cs) from Parallelism Curves in 48 De-identified Samples

|  | Inhibitor Present on Bethesda Assay | Inhibitor Absent on Bethesda Assay |
|---|---|---|
| Screening test positive for inhibitor (Ps/Cs ratio < 0.45) | 24 | 2 |
| Screening test negative for inhibitor (Ps/Cs ratio > 0.45) | 0 | 22 |

TABLE 2

Validation Studies: Statistical Analysis of Inhibitor
Screen Utilizing a Ratio of Patient to Control
Slopes of <0.45 from Parallelism Curves

| Statistic | Percent |
|---|---|
| Sensitivity | 100% |
| Specificity | 91.6% |
| Predictive Value of Positive Screening test for an Inhibitor (ratio < 0.45) | 92.3% |
| Predictive Value of Negative Screening test for an inhibitor (ratio > 0.45) | 100% |

Thus, it will be recognized from the foregoing that the disclosures herein provide a validated screening tool for detecting the presence of an inhibitor to Factor VIII during routine FVIII assays. This method has is adaptable for screening for the detection of inhibitors to other specific clotting factors such as FIX, lupus anticoagulants, and the presence of the newer oral anticoagulants which directly inhibit Factor Xa or thrombin.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein. To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. In some instances, the approximating language may correspond to the precision of an instrument or the conditions of the testing for measuring the value.

While the invention has been described through specific embodiments, routine modifications will be apparent to those skilled in the art and such modifications are intended to be within the scope of the present invention.

The invention claimed is:

1. A method of treating a patient having a condition associated with the presence of a Factor VIII inhibitor in a patient sample, the method comprising:
    generating a patient curve associated with the patient sample, the patient curve having a patient slope (Ps);
    generating a standard curve associated with a control sample, the standard curve having a control slope (Cs), wherein the patient curve and the standard curve are generated by plotting a plurality of clotting time points for a series of dilutions of the patient sample and the control sample relative to a Factor VIII clotting activity;
    determining a Ps/Cs parallelism ratio as being less than 0.45;
    determining, with a sensitivity of 100%, the presence of the Factor VIII inhibitor in the patient sample, and administering to the patient at least one agent for treatment of the condition associated with the presence of the Factor VIII inhibitor,
    wherein the at least one agent comprises one or more of 1-deamino-8-d-arginine vasopressin; human factor VIII; porcine factor VIII; an FVIII bypassing agent; an activated prothrombin complex concentrate; a nonactivated prothrombin complex concentrate; factor Xa, VIIa, or a recombinant version thereof of the patient; an agent used for immunosuppression: an antifibrinolytic; or a target anticoagulant.

2. The method of claim 1, wherein the Ps/Cs parallelism ratio is determined by a microprocessor in electronic communication with a clotting detection machine.

3. The method of claim 2, further comprising the step of:
    producing an output by the microprocessor, the output being capable of perceived visually or audibly by a human user or as digital information readable by a computer, wherein the output comprises an indication of the Ps/Cs parallelism ratio.

4. The method of claim 1, wherein the condition is hemophilia A.

5. The method of claim 1, wherein the condition is an autoimmune disorder.

6. The method of claim 1, wherein the at least one agent is one or more of the following: the human factor VIII, the porcine factor VIII, and the FVIII bypassing agent.

7. A method of treating a patient in having an autoimmune disorder associated with the presence of a Factor VIII inhibitor in a patient sample, the method comprising:
    generating a patient curve associated with the patient sample, the patient curve having a patient slope (Ps);
    generating a standard curve associated with a control sample, the standard curve having a control slope (Cs), wherein the patient curve and the standard curve are generated by plotting a plurality of clotting time points for a series of dilutions of the patient sample and the control sample relative to a Factor VIII clotting activity;
    determining a Ps/Cs parallelism ratio that is less than 0.45;
    determining the presence of the Factor VIII inhibitor in the patient sample with 100% sensitivity based on the determined Ps/Cs parallelism ratio; and
    administering to the patient one or more agents for treatment of the autoimmune disorder associated with the presence of the Factor VIII inhibitor, wherein the one or more agents include human factor VIII, porcine factor VIII, or an FVIII bypassing agent.

8. The method of claim 7, wherein the FVIII bypassing agent comprises an activated prothrombin complex concentrate Xa, a recombinant version of activated prothrombin complex concentrate Xa, an activated prothrombin complex concentrate VIIa, or a recombinant version of activated prothrombin complex concentrate VIIa.

9. The method of claim 7, further comprising:
    administering to the patient one or more immunosuppression agents for treatment of the autoimmune disorder, wherein the one or more immunosuppression agents include prednisolone cyclophosphamide, azathioprine, vincristine, mycophenolate mofetil, 2-chlorodeoxyadenosine, Cyclosporine A, or any combination thereof.

10. The method of claim 7, further comprising:
   detecting of the presence of alloantibodies in the patient sample; and
   diagnosing the patient with hemophilia A as the autoimmune disorder based at least in part on the determination that the Ps/Cs parallelism ratio is less than 0.45 and the detection of the presence of the alloantibodies in the patient sample.

11. The method of claim 10, wherein diagnosing the patient with hemophilia A comprises diagnosing the patient with congenital hemophilia A or acquired hemophilia A.

12. The method of claim 10, further comprising:
   administering to the patient one or more additional agents for treatment of hemophilia A, wherein the one or more additional agents include rituximab, cyclophosphamide, intravenous immunoglobulin (IVIG), or prednisolone.

13. The method of claim 7, further comprising:
   detecting of the presence of lupus anticoagulants in the patient sample; and
   diagnosing the patient with lupus as the autoimmune disorder based at least in part on the determination that the Ps/Cs parallelism ratio is less than 0.45 and the detection of the presence of the lupus anticoagulants in the patient sample.

14. The method of claim 7, further comprising:
   after administering the one or more agents to the patient for treatment of the autoimmune disorder, monitoring progress of the treatment by:
      generating a second patient curve associated with a second patient sample, the second patient curve having a second patient slope ($Ps^1$);
      generating a second standard curve associated with a second control sample, the second standard curve having a second control slope ($Cs^1$),
         wherein the second patient curve and the second standard curve are generated by plotting a second plurality of clotting time points for a second series of dilutions of the second patient sample and the second control sample relative to a second Factor VIII clotting activity;
      determining a $Ps^1/Cs^1$ parallelism ratio;
      responsive to determining that the $Ps^1/Cs^1$ parallelism ratio has increased relative to the Ps/Cs parallelism ratio, determining that the administration of the one or more agents to the patient is effective for treatment of the autoimmune disorder; and
      responsive to determining that the $Ps^1/Cs^1$ parallelism ratio has not increased relative to the Ps/Cs parallelism ratio, administering a plasmapheresis treatment or an immunoadsorption treatment to the patient for treatment of the autoimmune disorder.

15. The method of claim 14, further comprising:
   after administering the plasmapheresis treatment or the immunoadsorption treatment to the patient, administering to the patient an effective amount of additional human factor VIII or additional porcine factor VIII to achieve hemostasis in the patient bloodstream.

16. The method of claim 14, further comprising:
   responsive to determining that (i) the administration of the one or more agents is effective for treatment of the autoimmune disorder and (ii) that the $Ps^1/Cs^1$ parallelism ratio is less than 0.45, continuing administering to the patient the one or more agents for treatment of the autoimmune disorder.

* * * * *